(12) United States Patent
Tennison (10) Patent No.: US 8,718,792 B2
(45) Date of Patent: May 6, 2014

(54) SYSTEM AND METHOD OF REPAIRING OF NEURAL NETWORKS

(75) Inventor: Tamara Tennison, Virgina Beach, VA (US)

(73) Assignee: Neuron Networks Restored, LLC, Virgina Beach, VA (US)

( * ) Notice: Subject to any disclaimer, the term of this patent is extended or adjusted under 35 U.S.C. 154(b) by 576 days.

(21) Appl. No.: 12/952,199

(22) Filed: Nov. 23, 2010

(65) Prior Publication Data

US 2012/0065455 A1 Mar. 15, 2012

Related U.S. Application Data

(60) Provisional application No. 61/263,544, filed on Feb. 19, 2010.

(51) Int. Cl.
*A61N 1/00* (2006.01)
*A61N 1/05* (2006.01)

(52) U.S. Cl.
CPC .......... *A61N 1/0551* (2013.01); *A61H 2201/10* (2013.01)
USPC ............................ 607/118; 606/152; 128/897

(58) Field of Classification Search
USPC ............ 600/9–15; 607/1, 2, 48–50, 115–118; 606/152
See application file for complete search history.

(56) References Cited

U.S. PATENT DOCUMENTS

| 2007/0067883 A1* | 3/2007 | Sretavan ....................... 977/908 |
| 2008/0208268 A1* | 8/2008 | Bartic et al. ...................... 607/2 |

* cited by examiner

*Primary Examiner* — Charles A Marmor, II
*Assistant Examiner* — Carrie R Dorna
(74) *Attorney, Agent, or Firm* — Kimberly A. Chasteen (57) ABSTRACT

A method and system for re-establishing a pathway in a damaged or severed neural network includes an imaging device, an alignment device and a treatment device. An accurate image of the damaged neural network is created. An alignment device imparts wave energy into a damaged region of the neural network to direct re-growth axons into a remaining endoneurial tube to direct axon growth back to the correct targets to re-establish the severed neural network.

13 Claims, 6 Drawing Sheets

SYSTEM AND METHOD OF REPAIRING OF NEURAL NETWORKS

CROSS REFERENCE TO RELATED APPLICATION

The present application claims priority from U.S. Provisional Application Ser. No. 61/263,544, filed Nov. 23, 2009.

BACKGROUND OF THE INVENTION

1. Field of the Invention

The present invention relates to a system for treating damaged or severed neural networks within the body, and, more particularly to provide system with a neurostimulator that optimizes the environment for maximum re-growth potential of nerve cells.

2. Description of Related Art

It is known that damaged nerve cells, "neurons" may repair or heal themselves to re-establish neural networks. For purposes of this disclosure, the neural networks discussed herein relate the peripheral nerve cells. It should be recognized that the use of the techniques and technologies discussed herein, may be used to treat other nerve cells in the Central Nervous System (CNS) and brain. However, the primary objective of the invention is directed towards repairing the neural pathways of the Peripheral Nervous System (PNS).

There are many neural networks in the PNS throughout the body. These pathways carry nerve impulses that control various body functions and movements. Likewise, sensory feedback is also provided to the brain through these neural networks. When damaged or severed, a neural network fails to relay a nerve impulse from or to the brain. This break in a neural network results in the loss of a body function, movement, or sensory ability. An aim of the present invention is to re-establish a damaged peripheral nerve pathway such that nerve impulses can be relayed between a distal end of, a neural network and the brain.

An aim of the invention is to repair a neuron that includes a severed axon. If the body of the neuron is destroyed, it will not regenerate itself. In the case where a neuron, is destroyed, the destroyed neuron may be bypassed by causing axons from, a healthy proximal or distal neuron to grow around the destroyed neuron and to reconnect to the dendrites of the first healthy neuron distal from the destroyed neuron. After injury occurs to a neuron and, if the neuron body has not been destroyed, the proximal end of a severed axon begins to sprout new Schwan cells through, restored connections. The proximal axons are able to re-grow as long as the cell body is left intact and only the axons have been severed. If these new growth axons reach neurolemmocytes in the endoneurial channel, the severed neural pathway may be reestablished such that nerve impulses can be relayed through the newly established region of the neural network. It is to this end that, the present invention is practiced.

When severed, the distal end of any severed axons experience Wallerian degeneration within hours of the injury. During this process, the severed axons and myelin degenerate, but the endoneurium remains. Endoneurium is a delicate connective tissue that holds the nerve fibers together and supports them within the peripheral nerves. A tube of endoneurium material remains after the distal end of the severed axon degenerates. If an end of a regenerated axon reaches a remaining endoneurium of the severed or distal nerve end, the regenerating axon will grow through the remaining endoneurial tube to direct axon growth back to the correct targets to re-establish the severed neural network. It is this process that the invention aims to exploit in reestablishing a neural pathway.

It is a primary aim of the present invention to teach a system and method for promoting or regenerating axons through a use of creating a standing wave of energy that oscillates at a particular frequency unique to a damaged nerve cell. This standing wave energy is created between severed ends of a peripheral nerve. The wave energy may be light or sound energy. The terms "proximal end" and "distal end" of the severed nerve are defined with respect to the Central Nervous System.

It is an object of the invention to teach a system that comprises an imaging device that creates an accurate image of the location of severed ends of an axon. The device includes an alignment device that aligns the severed ends of the axon in proximity to one another. A treatment device imparts at least positive stimuli onto a growth cone on the proximal end of the severed axon to cause the growth cone to grow towards a remaining endoneurial channel to reestablish a neural network.

It is a further object of the invention to teach a process whereby images of a severed axon are created and displayed in an electronic format. The images are used to locate the proximal and distal ends of the severed axon. Thereafter, the proximal end of the severed axon is aligned in substantial alignment with the distal end of the severed axon, if necessary. The damaged region of the axon is treated with one or more of wave energy, electrical stimulation, magnetic stimulation and/or light and/or sound energy from a treatment device that may comprise a probe.

Finally, it is an object of the present invention to accomplish the foregoing objectives in a simple and cost effective manner.

The above and further objects, details and advantages of the invention will become apparent from the following detailed description, when read in conjunction with the accompanying drawings.

SUMMARY OF THE INVENTION

The present invention addresses these needs by providing a method for treating a damaged neuron that comprises a severed axon having a proximal end and a distal end. The method is creating an image of a damaged region of a neural network that comprises the damaged neuron; aligning severed ends of the axon substantially near one another; and imparting energy into an end of a growth cone extending from the severed proximal end of the axon to cause the end of the growth cone to grow towards an endoneurial channel remaining from a degenerated portion of the distal end. The image is preferably created using an electronic imaging device and is preferably a 3-dimensional image. In a particularly preferred embodiment, the 3-dimensional image is created using a microprocessor. Prior to creating the image of the damaged region of a neural network, the damaged area may be treated with a stain. Preferably the method includes aligning the severed ends of the axon substantially near one another by imparting wave energy into and through tissue surrounding the damaged area of the neural network such that a new growth axon is aligned with an endoneurial channel. Alternatively, the severed ends of the axon substantially near one another are aligned by using a plurality of oscillators that vary a frequency input to guide the severed ends of the neural pathway close to one another or by cutting material surrounding the severed ends and moving the severed ends together through use of pressure waves to guide the severed ends of the neural pathway close to one another. Energy is preferably imparted into the end of the growth cone by means of at least one probe for stimulating the proximal end of the severed axon to cause it to grow towards the degenerated distal end such that a remaining tube of endoneurium material is penetrated by a re-grown end of the axon such that the neural pathway is re-established. The probe may include a thin needle-like end which penetrates the skin and emits energy and preferably, the probe includes a cluster of instruments such as electric field generators, magnetic field generators, light sources, oscillators, receivers and sound sources. Alternatively, energy may be imparted into the end of the growth cone by means of a plurality of oscillators. The energy emitted from the probe includes both destructive and nondestructive energy levels.

A machine that treats a severed axon of a neuron is provided. The machine includes a microprocessor for controlling a frequency of light and vibratory energy applied to the severed axon of the neuron, with the microprocessor including a member that stores instructions for operating the machine. The machine further includes a power switch for energizing the machine, a light source, a vibratory energy source; a frequency controller and at least one probe. The probe has a handle and including a heat dissipating material in, contact therewith, a first light that indicates a treatment session is occurring, a second light that indicates when a treatment session has ended, a crystal quartz tip surrounded by a reflective metal sheath.

A system for treating a damaged region of a neural network is disclosed. The system includes an image creating device that creates a three-dimensional image of a damaged region of the neural network that is to be treated, an alignment device that aligns ends of a severed axon with one another; and a treatment device that imparts energy into a growth cone extending from a proximal end of a severed axon.

BRIEF DESCRIPTION OF THE DRAWINGS

A more complete description of the subject matter of the present invention and the advantages thereof, can be achieved by reference to the following detailed description by which reference is made to the accompanying drawings in which.

DETAILED DESCRIPTION OF THE PREFERRED EMBODIMENT

The following detailed description is of the best presently contemplated mode of carrying out the invention. This description is not to be taken in a limiting sense, but is made merely for the purpose of illustrating, general principles of embodiments of the invention. The embodiments of the invention and the various features and advantageous details thereof are more fully explained with reference to the non-limiting embodiments and examples that are described and/or illustrated in the accompanying drawings and set forth in the following description. It should be noted that the features illustrated in the drawings are not necessarily drawn to scale, and the features of one embodiment may be employed with the other embodiments as the skilled artisan recognizes, even if not explicitly stated herein. Descriptions of well-known components and techniques may, be omitted to avoid obscuring the invention. The examples used herein are intended merely to facilitate an understanding of ways in which the invention may be practiced and to further enable those skilled in the art to practice the invention. Accordingly, the examples and embodiments set forth herein should not be construed as limiting the scope of the invention, which is defined by the appended claims. Moreover, it is noted that like reference numerals represent similar parts throughout the several views of the drawings.

Generally, the present invention relates to a system that includes several devices and process steps that are implemented for treating damaged or severed neural networks within the body. It is well known that neurons are electrically excitable and damage to these networks can cause numerous diseases such as Parkinson's, Huntington's or Alzheimer's. Injury, such as spinal cord damage or blows to the brain, can cause damage to neurons as well, see "The Life and Death of a Neuron" (http://www.ninds.nih.gov/disorders/brain_basics/ninds_neuron.htm) or "Neuron" (http:en.wikipedia.org/wiki/Neuron), both incorporated herein by reference in their entireties. In this invention, the damaged or severed neural network is identified. An image, which is representative of a severed or damaged neural network, is produced to provide an accurate locale of the damaged portions of the neural network that are to be treated. If necessary, an accurate location of each severed ends of an axon(s) is located using an electronic imaging device. In one instance, a microprocessor creates a three dimensional analysis of the damaged neurons. Severed ends of axon(s) are aligned by imparting wave energy into and through the tissue surrounding the damaged area of the neural network such that a new growth axon is aligned with an endoneurial channel. That is, the ends, of severed nerve cells are aligned in proximity to one another such that axons grown from the proximal end of a severed nerve are directed to grow towards the neurolemmocytes in the endoneurial channel, to re-establish a severed neural network. Energy imparted into, the area surrounding the damaged nerve cell acts to push the severed ends of the axon into alignment with one another and to cause them to re-grow towards one another to establish a neural pathway. Thus, the invention aims to provide a neurostimulator that optimizes the environment for maximum re-growth potential of nerve cells. An end of a growth cone is steered to grow towards the remaining endoneurial channel, from a severed end of an axon.

THz electromagnetic waves are the focus of this invention. The method includes working in the meridians of the body that are ½ inch apart with a fiber optic needle encased in stainless steel, preferably with articulating prisms at the tip of the needle. This procedure, known as stylostixis, reopens the ion channels to restore growth that would normally occur in an electronic chemical process but in this method is produced through electromagnetic wavelengths.

The present invention is a system and method of re-establishing neural networks in the body. The system includes an imaging device or means that creates a 3-dimensional image of a broken region of a neural network including severed ends of an axon, extending from a neuron. A patient may be given a pharmacological mixture of a liquid which may contain protein or a glucose based radio pharmaceutical. The liquid may be taken orally or intravenously to illuminate electrical synapses in nerve cells for recording the frequency of the neurons surrounding the damaged or disconnected area(s) of the neural network. Once the frequencies of the nerve ells is recorded and fed into an oscillator, a microprocessor programmed with software measures mass energy, signal velocity, particle velocity, particle displacement and momentum to determine the appropriate frequency, accurate image and correct placement of the treatment probe or probes. The microprocessor may also calibrate the probe(s) to align signal patterns to create new growth and/or repair of the damaged nerve cells. This process may involve the use of harmonic resonance frequencies and, light waves to detect and/or repair the damaged cells. An alignment device or means is provided for aligning the severed ends of the axon such that a proximal end is aligned near a distal end. A treatment device or means includes at least one probe for stimulating the proximal end of the severed axon to cause it to grow towards the degenerated distal end such that a remaining tube of endoneurium material is penetrated by a re-grown end of the axon such that the neural pathway is re-established.

An imaging device includes a means that produces an accurate image representative of a damaged nerve cell. The image includes at least a three-dimensional rendering of the location of the damaged or severed area of the neural network. In one instance, the damaged area is treated with a stain prior to creating an image of it. Magnetic Resonance Imaging Machines may be utilized in creating the image of the damaged region of the neural pathway. Typically, any electronic device that can segregate between different types of human tissue may be utilized in creating an image of the damaged region.

The severed ends of the neural network are brought into close proximity with one another through various surgical techniques which may include the use of oscillatory means that impart wave energy into the damaged region of the neural network. In one instance, an alignment device includes oscillators that vary a frequency input to guide the severed ends of the neural pathway close to one another. The oscillators may also be used elicit a growth response from a damaged nerve cell. The present invention first causes the ends severed ends of the severed nerve to be brought together in close proximity and thereafter a unique frequency is directed towards the proximal end of the nerve to cause it to grow towards the distal end of the severed nerve.

In one instance a treatment device, which may comprise part of the imaging device, includes oscillators that create positive stimuli to encourage a direction of growth for a growth cone growing from a proximal end of the severed axon. A resonance frequency, unique to the damaged nerve cell, is determined and thereafter used to as a neurostimulator to trigger a response in a re-growing end of an axon to cause it to grow in a particular direction. The particular direction is an accurate pathway, preferably the shortest pathway, between an injured neuron that includes a severed axon and the closest neuron on the distal end of the injured or severed region and having dendrites that connect to the severed end, of the axon. In this manner, the amount of recovery time for a nerve injury is advantageously shortened. Other wave energy may be imparted to create a pathway through which the re-grown axon is directed into the endoneurial tube left by a degenerated end of a severed axon.

In one instance, the treatment device comprises a probe that includes a thin needle-like end which penetrates the skin and emits energy into a damaged region of the body to stimulate axon growth to recreate a neural pathway enabling nerve impulses to be transmitted from the CNS to a distal end of the neural pathway. The probe may include a cluster of instruments, including, but not limited to, electric field generators, magnetic field generators, light sources, oscillators, receivers and sound sources. Energy emitted from the probe may include both destructive and nondestructive energy levels.

The probe may comprise a crystal oscillator that sets up a particular electric or magnetic field within the damaged region of the nerve cell to cause polarization of particular cell materials. That is, positive and negative domains within the cellular material may be aligned in a particular direction or periodically flipped from one direction to the other such that a particular portion of the cell may be either positively or negatively charged. The charge may be changed to an opposite charge by reorienting the electric or magnetic field emitted by the probe. Otherwise the probe may include a light source, preferably a light emitting diode that emits a particular pulsed light that stimulates a damaged region of a nerve cell. Other light sources, such as sunlight or lamps of various light wave frequencies may be utilized in repairing the nerve cells.

The probe may also comprise an energy imparting device such as an oscillator that imparts wave energy into the tissue surrounding the severed axon to create a moving or standing wave of energy. Other electrical stimulators may be used to stimulate growth of a growth cone from the proximal severed end of the axon. Oscillators may be calibrated according to each damaged neuron. Moreover, oscillators may be used to treat the damaged region of the neural network. In another embodiment, a light and/or sound source may be used to stimulate growth of the severed end of the neuron. The light and/or sound source may emit a continuous or pulsed source of light and/or sound.

The method taught by the present invention includes a method of promoting nerve repair, comprising the steps of providing an imaging device that creates a computer model of a damage nerve region. The step of imaging the damaged region may include having the patient drink a solution of potassium, sodium and chlorine. A proximal severed end of a neuron is stimulated to cause a growth cone to grow towards an endoneurial channel remaining from a degenerated distal end of the severed axon. In one instance, a standing wave is created by an oscillator that imparts energy into the region between severed ends of the nerve cell. This standing wave guides a newly formed growth cone from the proximal end, of the severed axon into the endoneurial channel which will cause them to make contact with the neurolemmocytes to reestablish a neural pathway. This process enables a quicker recovery of the damaged neuron. The oscillator may include a sound and/or light generating mechanism.

In one instance, the steps include immobilizing the affected area and scanning the area to determine a location of the damaged or, severed nerve ends. If ends of an axon are severed then the ends are aligned by cutting material surrounding them and moving the ends together through use of pressure waves. Destructive energy may be imparted into areas where material is to be destroyed or cut. An image created by an imaging device is referenced to determine the extent of damage to the neural network. Energy is imparted by the system to treat the damaged neural region. Acupuncture needles comprising silicon fibers may also be placed in the energy meridians of the nervous system and body to administer treatment.

Now referring to figures, FIGS. 1A-1C and 2A-2E show a healthy part of a neural network. In the PNS, a neural network includes neuron 100A that relays muscle control and sensory information from and to the CNS. This information is relayed from one neuron 100A to another neuron 100B by way of an axon 105A having ends synaptic gap 115 to relay information to dendrites 110 of an adjoining neuron 100B. The axon 105A includes a healthy myelin sheath 106A.

Figure 1A:
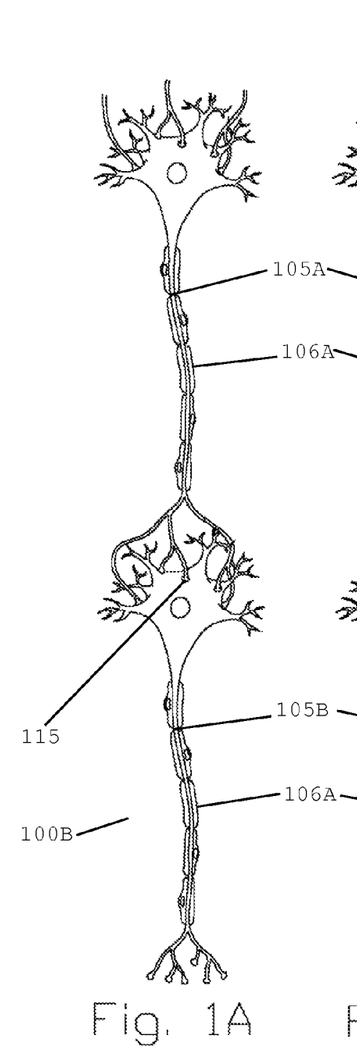
FIGS. 1A-1C show a portion of a neural network that is injured and treated in accord with the present invention.
Figures 1B, 1C:
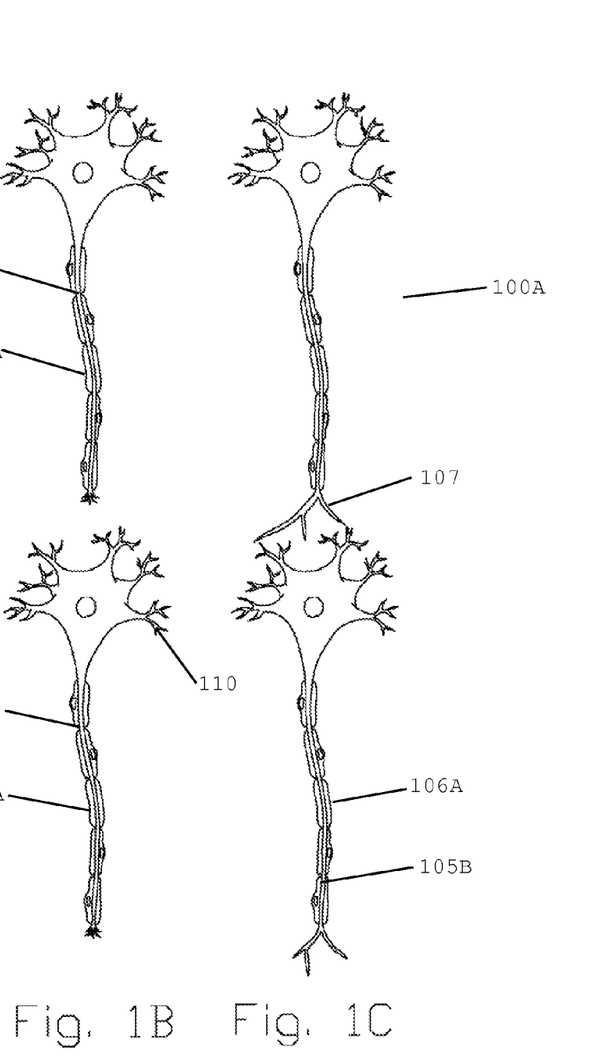

When injury occurs to the neural network, the information may fail transmitted between the neurons 100A, 100B. For example, FIG. 1B shows that axon 105A is severed into two pieces. In an effort to reestablish communications with the distal end of the neural network, the proximal end of the severed axon 105A will sprouting growth cones 107 as shown in FIG. 1C. The distal end 105B of the severed axon, including myelin sheath 106B begins to degenerate until only an endoneurial tube 120 remains. Should one of the growth cones 107 reach the remaining endoneurial tube 120, the neuron 100A will reestablish neural contact with the neuron 100B. The present invention aims to realign the ends of the severed axon in substantial proximity to one another and thereafter stimulate an end of a growth cone causing it to grow towards remaining endoneurial tube 120 to reestablish the neural network.

Figures 2A, 2B:
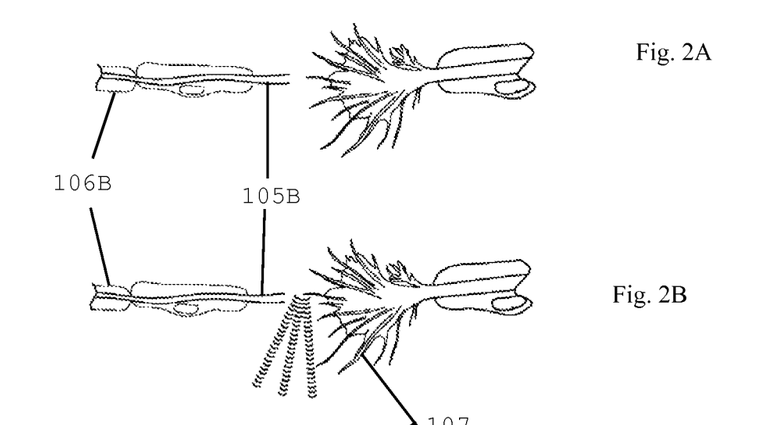
FIGS. 2A-2E show a severed end of an axon having a plurality of growth cones one of which is subjected to a treatment that causes it to grow towards an endoneurial channel that remains from a severed end of the axon.

FIGS. 2A-2E show an enlarged view of the severed end of the axon having a plurality of growth cones one of which is subjected to a treatment that causes it to grow towards an endoneurial channel that remains from a severed end of the axon. In FIG. 2A, a proximal severed end 105A of an axon has a plurality of growth cones 107. A location of each of the axon's severed ends is determined by subjecting the damaged area to an imaging means. The imaging means may include an MRI machine or other such device that creates an accurate image of injured area. Images created by the imaging device are used in determining where wave energy is applied and the frequency of said wave energy that is applied.

In a preferred embodiment, a plurality of images are taken of the are, from different locations about the injured area to create a three-dimensional representation of the severed ends of the axon to determine where the remaining endoneurial tube 120 located. The operator or computer assisted programming views the growth cones and selects an appropriate one to be directed into endoneurial channel 120 that remains from the severed end of the axon. Wave energy may be utilized as a neurostimulator to cause a particular part of the growth cone 107 to grow in a particular direction. Destructive wave energy may also be introduced into the injured region surrounding the damaged neural pathway to destroy objects that may be between a growth cone 107 and the endoneurial tube 120.

Figure 2C:
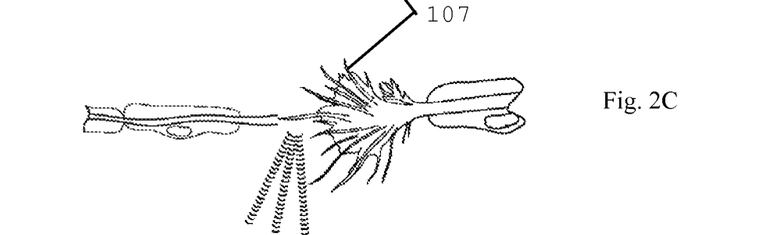
Figure 2D:
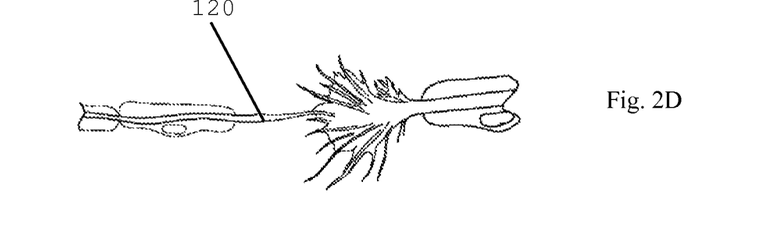
Figure 2E:
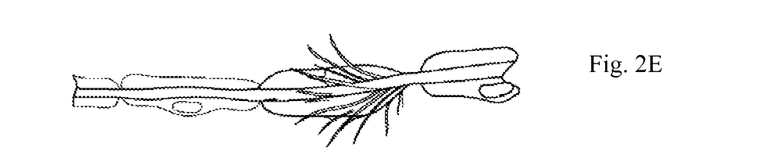

FIG. 2B represents the application of wave energy from three sources, each of which may be housed in a probe or treatment machine as discussed hereinafter. After a appropriate growth cone 107 is selected, wave energy is directed into a particular face or region of the growth cone. This wave energy comprises either positive or negative stimuli that encourages the growth cone 107 to grow in a particular direction. As shown in FIG. 2C, this stimuli is moved towards the endoneurial tube 120 to cause the selected growth cone 107 to grow into an open end thereof. Once the growth cone 107 makes contact with the endoneurial tube 120, it will quickly grow into the tube and reestablish the neural pathway, as shown in FIG. 2D. The myelin sheath 106B will regenerate over the axon as shown in FIG. 2E.

Figure 3:
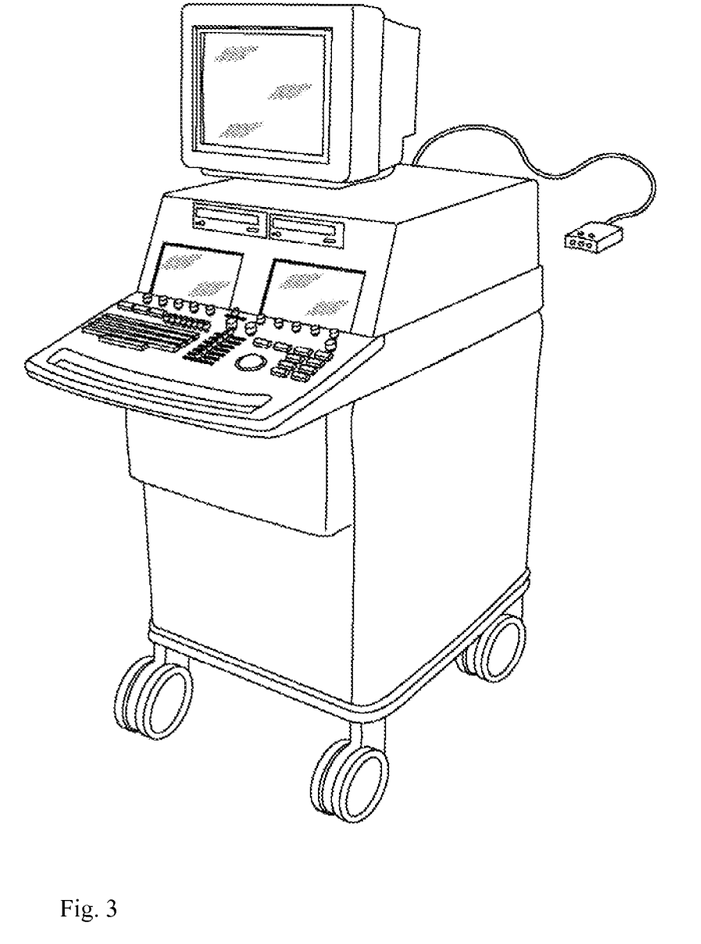
FIG. 3 is a perspective view of a treatment machine for use in repairing a damaged nerve cell.

FIG. 3 is a perspective view of a treatment machine for use in repairing a damaged nerve cell. In one instance, the machine includes a power switch, a light source, a plurality of probe connectors, a frequency controller and a readout for indicating the frequency of the light or vibratory energy. The probes include a handle arranged against a granite member that diffuses heat created by the transmission of both light and vibratory energy. Two lights are provided on each probe. One light is green; the other is red. The green light indicates that the treatment session should be continued. The red light is a warning light to indicate when the treatment has been concluded. Typical treatment times are forty-five seconds to one hour. In a typical machine, three probes are included. Each probe has a unique frequency and is provided in different widths and lengths. Each probe tip comprises a silicon quartz crystal that is surrounded by a reflective metal sheath. The probe may be used in conjunction with a table that comprises a magnetic field for treating a damaged neural network. A calibration circuit may be provided in each probe along with a timer circuit.

Figure 4A:
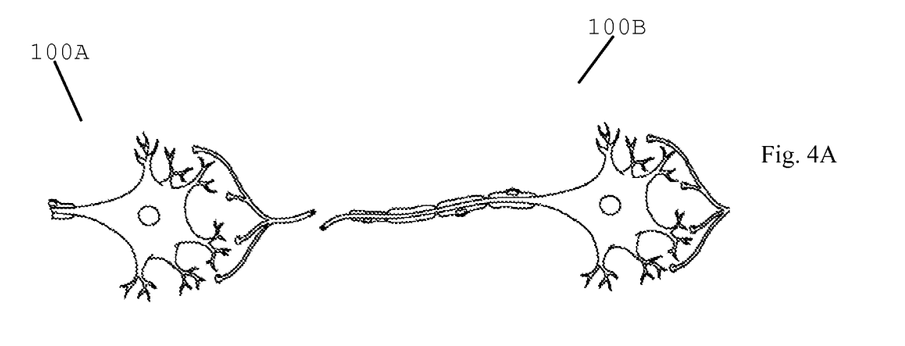
FIGS. 4A-4C show a severed axon having a proximal and distal end that are aligned in substantial proximity with one another prior to treating the proximal end.
Figure 4B:
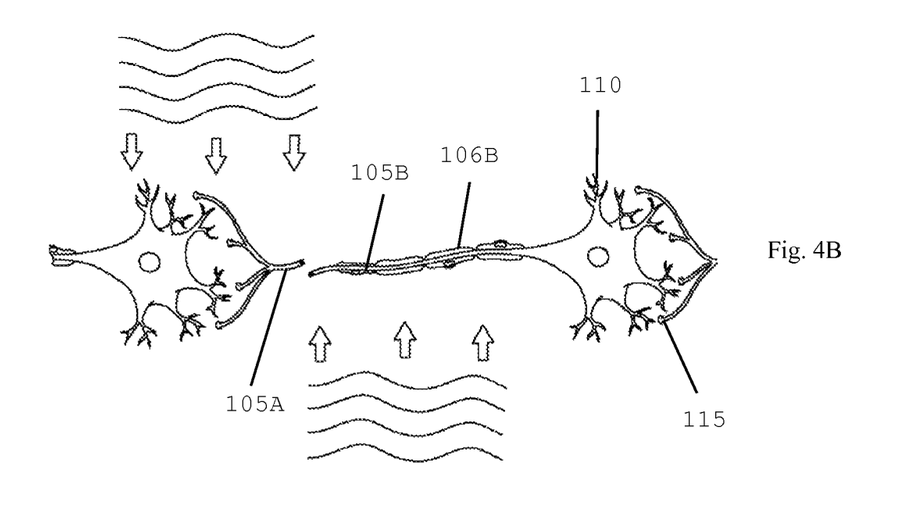
Figure 4C:
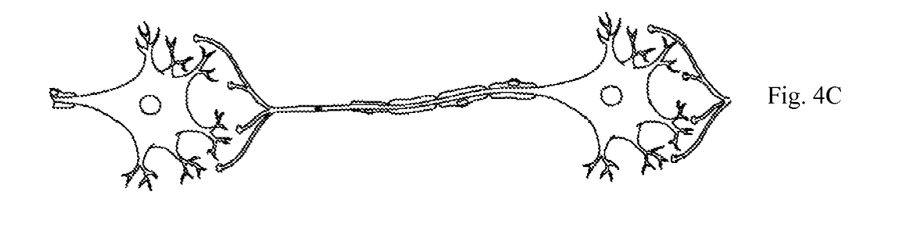

FIGS. 4A-4C show a severed axon having a proximal and distal end that are aligned in substantial proximity with one another prior to treating the proximal end. As can be understood from these drawings, the severed ends of the nerve cells may be aligned using vibratory energy.

Figure 5:
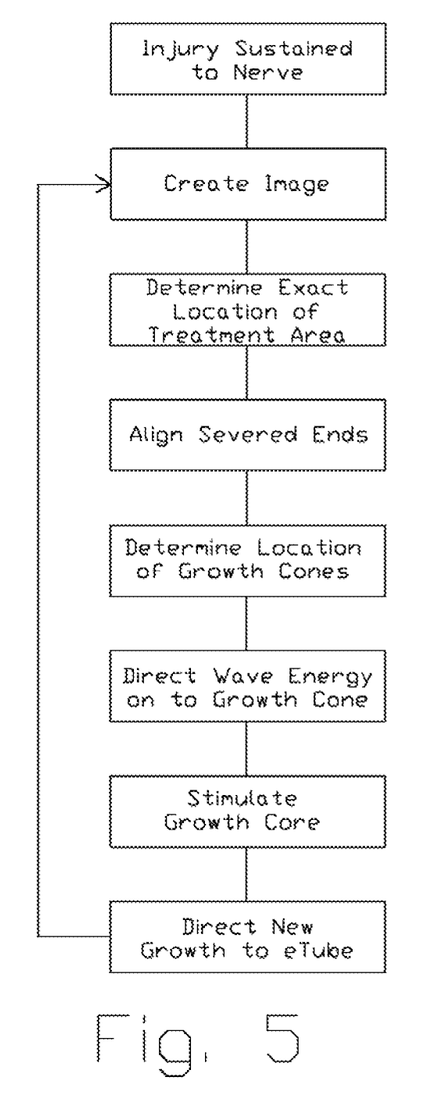
FIG. 5 is a flowchart showing the process steps in practicing the invention.
Figure 6:
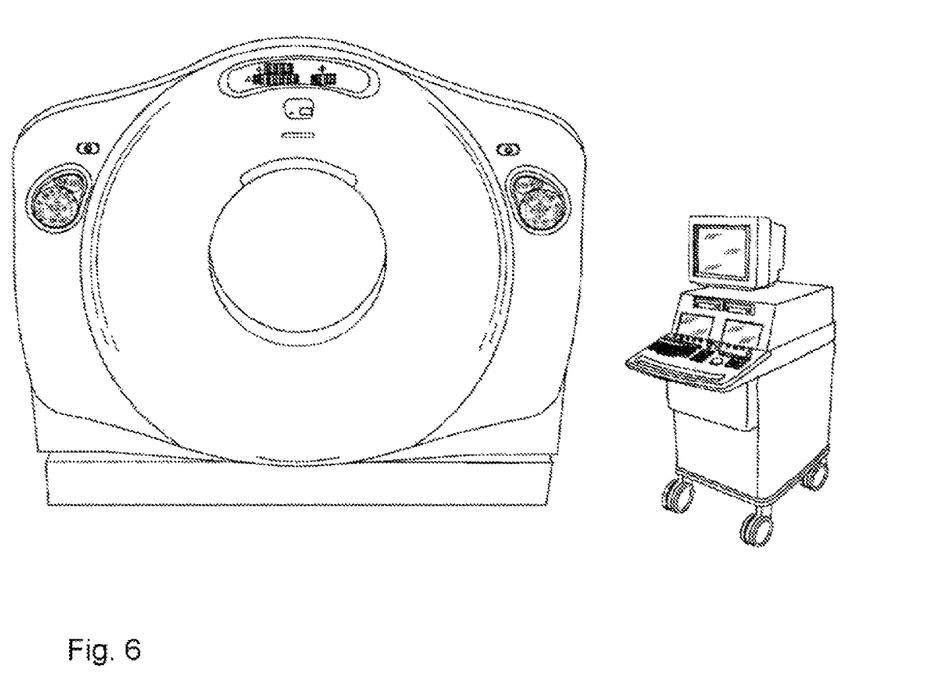
FIG. 6 shows a combination imaging and treatment machine.

FIG. 5 is a flowchart showing the process steps in practicing the invention. After an injury to a neural network has been sustained, an image is created with an imaging device such as a magnetic resonance imaging machine. As previously discussed, a pharmacological mixture may be introduced into the patient to aid in the imaging step. The exact location of the severed nerve cells is determined. If necessary, the severed ends of the nerve cells are aligned in proximity to one another. The location of growth cones may also be determined. Wave and light energy may be directed onto the growth cones to cause them to grow into the endoneurial channel to reestablish a connection in the nerve cell.

In a preferred embodiment of the present invention, terahertz (THz) electromagnetic waves are used. Research towards the development of electronic oscillators capable of reaching THz frequencies pushes out the limits of high-speed electronics and are used in the probes (see web site, "Michigan Engineering/Terahertz Electromagnetic Waves" at http://www.engin.umich.edu/research/cuos/ResearchGroups/US/Research/Terahertz_Electromagnetic_Waves.html), incorporated herein by reference in its entirety. The nonlinear properties of a crystal are used to generate a wave. A short laser pulse hits the crystal, generally zinc telluride (ZnTe) or lithium niobate ($LiNbO_3$). The laser pulse induces a second-order nonlinear polarization, proportional to the intensity envelope of the laser pulse. For ultrafast pulses (on the order of 100 femtoseconds or shorter) the generated polarization peaks around a few terahertz. The terahertz field measured is the radiated field of the polarization. Periodically-poled LiNbO3 (PPLN) generates ½ of a wave in each domain of the crystal. Stacking together many alternating domains produces a THz waveform consisting of many oscillations. Further basis for this method is shown at "Fiber Optic Sensors with Mechanical Resonators in which the Output Signal is Amplitude of Vibration" (see http://physics-animations.com/English/analog.htm) incorporated herein by reference in its entirety.

Obviously, many modifications may be made without departing from the basic spirit of the present invention. Accordingly, it will be appreciated by those skilled in the art that within the scope of the appended claims, the invention may be practiced other than has, been specifically described herein. Many improvements modifications, and additions will be apparent to the skilled artisan without departing from the spirit and scope of the present invention as described herein and defined in the following claims.

What is claimed is:

1. A method for treating a damaged neuron that comprises a severed axon having a proximal end and a distal end, said method comprising:

creating an image of a damaged region of a neural network that comprises the damaged neuron;

aligning severed ends of the axon substantially near one another by cutting material surrounding the severed ends and moving the severed ends together through use of pressure waves to guide the severed ends of the axon close to one another while viewing the image; and imparting energy into an end of a growth cone extending from the severed proximal end of the axon to cause the end of the growth cone to grow towards an endoneurial channel remaining from a degenerated portion of the distal end.

2. The method for treating a damaged neuron of claim 1 wherein the image is created using an electronic imaging device.

3. The method for treating a damaged neuron of claim 1 wherein the image is a 3-dimensional image.

4. The method for treating a damaged neuron of claim 3 wherein the 3-dimensional image is created using a microprocessor.

5. The method for treating a damaged neuron of claim 1 wherein, prior to creating the image of the damaged region of a neural network, the damaged area is treated with a stain.

6. The method for treating a damaged neuron of claim 1 wherein the severed ends of the axon substantially near one another are aligned by imparting wave energy into and through tissue surrounding the damaged area of the neural network such that a new growth axon is aligned with an endoneurial channel.

7. The method for treating a damaged neuron of claim 1 wherein the severed ends of the axon substantially near one another are aligned by using a plurality of oscillators that vary a frequency input to guide the severed ends of the axon close to one another.

8. The method for treating a damaged neuron of claim 1 wherein energy is imparted into the end of the growth cone via at least one probe for stimulating the proximal end of the severed axon to cause it to grow towards the degenerated distal end such that a remaining tube of endoneurium material, is penetrated by a re-grown end of the axon such that a neural pathway is re-established.

9. The method for treating a damaged neuron of claim 8 wherein the at least one probe includes a thin needle-like end which penetrates skin and emits energy.

10. The method for treating a damaged neuron of claim 8 wherein the at least one probe includes a cluster of instruments selected from the group consisting of electric field generators, magnetic field generators, light sources, oscillators, receivers and soul sources.

11. The method for treating a damaged neuron of claim 8 wherein energy is imparted into the end of the growth cone via a plurality of oscillators.

12. The method for treating a damaged neuron of claim 8 wherein the energy emitted from the at least one probe includes both destructive and nondestructive energy levels.

13. A system for treating a damaged region of a neural network, said system comprising:

an image creating device that creates a three-dimensional image of a damaged region of the neural network that is to he treated;

an alignment device that aligns ends of a severed axon with one another by cutting material surrounding the severed ends and moving the severed ends together through use of pressure waves to guide the severed ends of the axon close to one another; and a treatment device that imparts energy into a growth cone extending from of a severed axon.

* * * * *